(12) United States Patent
Yamaguchi

(10) Patent No.: US 8,922,561 B2
(45) Date of Patent: Dec. 30, 2014

(54) DATA PROCESSING DEVICE, DATA PROCESSING SYSTEM, AND DATA PROCESSING METHOD FOR IDENTIFYING DATA FROM BOTH LICENSED AND UNLICENSED DEVICES

(75) Inventor: Kohei Yamaguchi, Kanagawa (JP)

(73) Assignee: Panasonic Intellectual Property Corporation of America, Torrance, CA (US)

( * ) Notice: Subject to any disclaimer, the term of this patent is extended or adjusted under 35 U.S.C. 154(b) by 199 days.

(21) Appl. No.: 13/640,404

(22) PCT Filed: Dec. 22, 2011

(86) PCT No.: PCT/JP2011/007206
§ 371 (c)(1),
(2), (4) Date: Oct. 10, 2012

(87) PCT Pub. No.: WO2012/114414
PCT Pub. Date: Aug. 30, 2012

(65) Prior Publication Data
US 2013/0050221 A1 Feb. 28, 2013

(30) Foreign Application Priority Data
Feb. 21, 2011 (JP) .................. 2011-034485

(51) Int. Cl.
*G06T 11/00* (2006.01)
*G06K 11/00* (2006.01)
(Continued)

(52) U.S. Cl.
CPC .............. *G06F 19/322* (2013.01); *G06Q 50/22* (2013.01); *G06Q 50/24* (2013.01); *G06F 19/345* (2013.01); *G06F 19/3487* (2013.01); *A61B 5/024* (2013.01); *A61B 5/14507* (2013.01); *A61B 5/165* (2013.01); *A61B 5/4277* (2013.01)
USPC ....................................... 345/440; 345/440.1

(58) Field of Classification Search
None
See application file for complete search history.

(56) References Cited

U.S. PATENT DOCUMENTS 5,400,794 A * 3/1995 Gorman ................... 600/508
6,650,932 B1 * 11/2003 Menzie et al. ............. 600/513
(Continued)

FOREIGN PATENT DOCUMENTS

JP 2006-277219 10/2006
JP 2006-320444 11/2006
(Continued)

OTHER PUBLICATIONS

International Search Report issued Jan. 31, 2012 in corresponding International Application No. PCT/JP2011/007206.
(Continued)

*Primary Examiner* — David Zarka
*Assistant Examiner* — Jason Pringle-Parker
(74) *Attorney, Agent, or Firm* — Wenderoth, Lind & Ponack, L.L.P.

(57) ABSTRACT

The data processing device includes an acquisition unit that acquires a plurality of pieces of the same category of bio-information about the same person. The bio-information is measured with both a licensed first device and an unlicensed second device. A judgment unit judges whether each acquired piece of bio-information acquired in the previous acquisition was measured by the first device or the second device. A display processing unit displays with different display modes on the same screen, a first data group of a plurality of pieces of bio-information judged to have been measured with the first device and a second data group of a plurality of pieces of bio-information judged to have been measured with the second device. The data processing device identifies data when data from both licensed and unlicensed devices coexist.

7 Claims, 13 Drawing Sheets

(51) Int. Cl.
*A61B 5/02* (2006.01)
*G06F 19/00* (2011.01)
*G06Q 50/22* (2012.01)
*G06Q 50/24* (2012.01)
*A61B 5/024* (2006.01)
*A61B 5/145* (2006.01)
*A61B 5/16* (2006.01)
*A61B 5/00* (2006.01)

(56) References Cited

U.S. PATENT DOCUMENTS

| | | | |
|---|---|---|---|
| 2002/0131404 A1* | 9/2002 | Mehta et al. | 370/352 |
| 2003/0220582 A1* | 11/2003 | Zhu et al. | 600/549 |
| 2004/0186390 A1* | 9/2004 | Ross et al. | 600/532 |
| 2005/0151056 A1 | 7/2005 | Parks | |
| 2006/0084551 A1* | 4/2006 | Volpe, Jr. | 482/8 |
| 2009/0106050 A1 | 4/2009 | Ikeda et al. | |
| 2009/0112111 A1* | 4/2009 | Shimizu et al. | 600/520 |
| 2009/0216132 A1* | 8/2009 | Orbach | 600/485 |
| 2009/0227882 A1* | 9/2009 | Foo | 600/508 |

FOREIGN PATENT DOCUMENTS

| | | |
|---|---|---|
| JP | 2006-331202 | 12/2006 |
| JP | 2007-520063 | 7/2007 |
| JP | 2008-269652 | 11/2008 |
| JP | 2009-146340 | 7/2009 |
| JP | 2009-168731 | 7/2009 |
| WO | 2006/132106 | 12/2006 |

OTHER PUBLICATIONS

Hirofumi Yamamoto, "Reforms to streamline the approval system for medical devices", Gekkan Shiniryo, vol. 32, No. 2, Feb. 1, 2005, pp. 46-49 (with partial English translation).

* cited by examiner

FIG. 2

| Device name | Model number | Measurement classification | Unit | Authorization flag | Authorization number |
|---|---|---|---|---|---|
| Salivary amylase measuring device | A001 | Stress | KIU/L | 1 | 0123 |
| Simple pulse measuring instrument | B001 | Stress | Heart barometer | 0 | — |
| Low-frequency condenser microphone | B002 | Stress | Heart barometer | 0 | — |
| ... | ... | ... | ... | ... | ... |

| Information ID | Authorization flag | Measurement date and time | Classification | Measurement device name | Measurement unit | Measurement data |
|---|---|---|---|---|---|---|
| 0001 | 1 | 2010/12/01 09:00:15 | Stress | Salivary amylase measuring device | KIU/L | 12.0 |
| 0002 | 0 | 2010/12/01 09:01:05 | Stress | Simple pulse measuring instrument | Heart barometer | 50.0 |
| 0003 | 0 | 2010/12/01 09:30:35 | Stress | Simple pulse measuring instrument | Heart barometer | 60.0 |
| 0004 | 0 | 2010/12/01 10:00:35 | Stress | Simple pulse measuring instrument | Heart barometer | 59.0 |
| 0005 | 1 | 2010/12/01 10:00:50 | Stress | Salivary amylase measuring device | KIU/L | 20.0 |
| 0006 | 0 | 2010/12/01 10:20:50 | Stress | Simple pulse measuring instrument | Heart barometer | 72.0 |
| 0007 | 0 | 2010/12/01 10:55:50 | Stress | Simple pulse measuring instrument | Heart barometer | 52.0 |
| 0008 | 1 | 2010/12/01 11:02:50 | Stress | Salivary amylase measuring device | KIU/L | 15.0 |
| 0009 | 0 | 2010/12/01 11:30:45 | Stress | Simple pulse measuring instrument | Heart barometer | 55.0 |
| ... | ... | ... | ... | ... | ... | ... |

T200

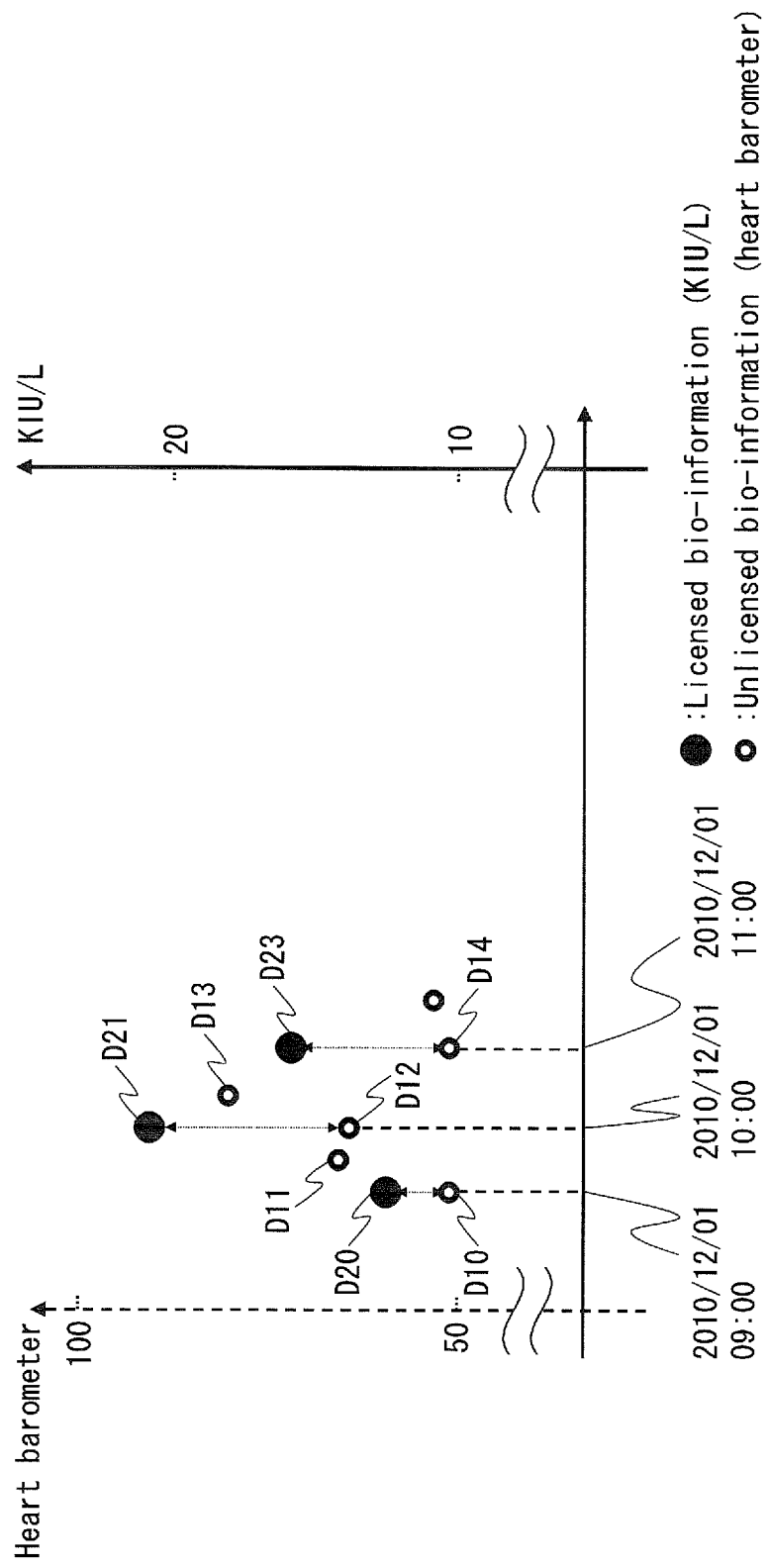

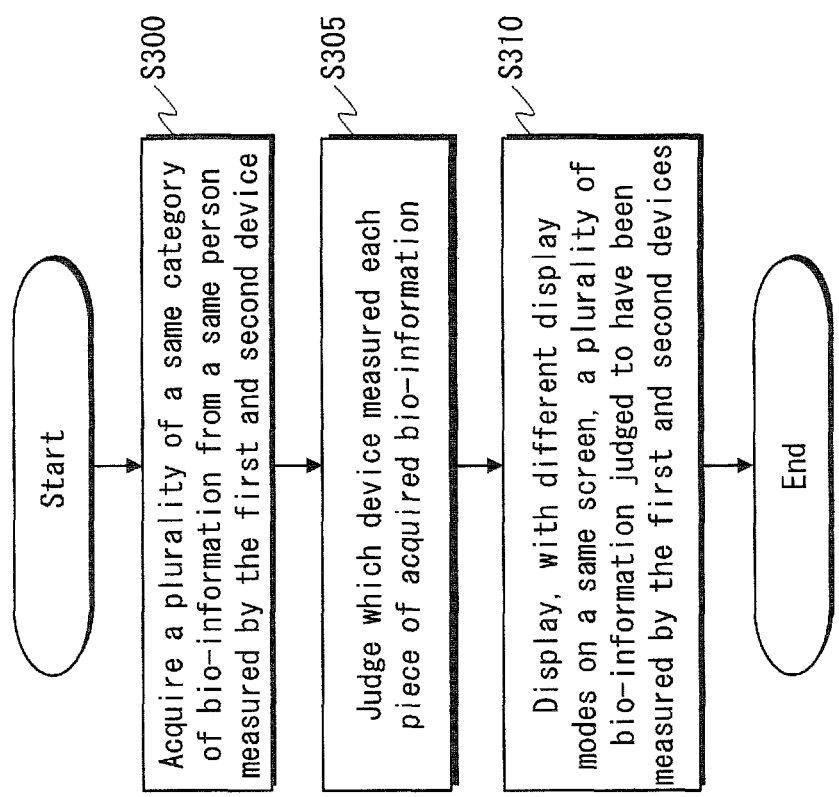

DATA PROCESSING DEVICE, DATA PROCESSING SYSTEM, AND DATA PROCESSING METHOD FOR IDENTIFYING DATA FROM BOTH LICENSED AND UNLICENSED DEVICES

TECHNICAL FIELD

The present invention relates to devices which have been licensed for manufacture by specific organizations, and to devices which assemble and display data from unlicensed devices.

BACKGROUND OF INVENTION

1. Background Art

In recent years, the combining of information equipment and medical care IT technologies has been increasing. In other words, the coordination of information equipment and sensors which collect bio-information such as the condition of human saliva, pulse rate, etc, and the use of information equipment to refine data and provide services based upon such data can be predicted to become increasingly prosperous in the future.

However, the Pharmaceutical Affairs Law regulating the manufacturing, importation and sale of drugs and medical devices drives a wall between medical care and the use of devices to measure bio-information for healthcare purposes. In other words, in order to use bio-information measured by a device to make medical judgments, restrictions decree that the aforementioned device must receive authorization in accordance with the Pharmaceutical Affairs Law.

At present, it is typical for medical and health related equipment produced with authorization to be used at home or in a medical institution with measuring devices specialized for bio-information. In the future however, it is predictable that the implementation of such functions in portable terminals, or the cooperation between multiple measuring devices and information terminals will result in information terminals acquiring a variety of bio-information, and the provision of a diverse range of health related services. By providing portable terminals, for example portable information terminals with bio-information measuring functions, it will become possible to measure bio-information anywhere and at any time.

In this way, once it becomes possible to measure bio-information from devices which can be used in the home or at a medical institution, and also from devices which can be used anywhere, then demand will arise for a combining and displaying of measurement data received from a plurality of measuring devices so that a user may observe changes in bio-information. A method is shown in Patent Literature 1 wherein measurement data is received from a plurality of measurement devices then regulated by each measurement device, the changes in data then being displayed to a user.

CITATION LIST

Patent Literature

[Patent Literature 1]
WO 2006/132106

SUMMARY OF INVENTION

Incidentally, it is difficult for portable information terminals, of which cellular telephones are an example, to comply with the Pharmaceutical Affairs Law which requires a lengthy period of time after application to receive authorization, as portable information terminals have complex functions and new models are released in a rapid cycle. In this case, attempting to provide portable information terminals with functions in line with the cycle of new model releases without receiving Pharmaceutical Affairs Law authorization will result in the provision of simple measuring functions. From such unlicensed, simple devices, less reliable data can be gathered compared to devices which comply with the Pharmaceutical Affairs Law.

Ultimately, measurements made using only those devices which comply with the Pharmaceutical Affairs Law will lack portability, being therefore inconvenient. Also, measurements made using only unlicensed devices will lack data reliability. For these reasons, there is a demand for the coexistence of data from licensed devices and unlicensed devices alike, in order to provide both convenience and data reliability.

In the case of such coexistence, a clear distinction must be made as to which device provides which measurement data. The reason for this is that a medical professional must be clear as to whether or not the displayed data may be used for making medical judgments.

However, in the case of such an intermingling of data received from a device licensed by the Pharmaceutical Affairs Law with data received from an unlicensed device, the structure shown in Patent Literature 1 thus far only holds device identification and user identification as the bio-information, and only performs identification of bio-information to link devices with users and make a display in accordance with the identification. Therefore, it is not possible to discern which data came from a licensed device and which data came from an unlicensed device.

For medical professionals, only data received from a licensed device may be used to make medical judgments. Therefore, if it is not possible to identify the data, then it is not feasible for the data as a whole to be used when it contains data from unlicensed devices.

Accordingly, in view of the above problem, it is an aim of the present invention to provide a data processing device, data processing system and data processing method to distinguish between data from licensed and unlicensed devices when data from both devices coexist.

In order to solve the above problems, the present invention is a data processing device comprising: comprising: an acquisition unit that acquires a plurality of bio-information pieces of a single category about a single person, the bio-information pieces including (i) pieces measured by a measurement device, the measurement device being a first device that is a medical device licensed for manufacture by a certain organization, (ii) pieces measured by a measurement device, the measurement device being a second device that is a medical device unlicensed for manufacture by the certain organization; a judgment unit that judges whether each acquired bio-information piece was measured by the first device or by the second device; and a display processing unit that displays on a same screen, with different visual representations, a first data group representing a plurality of bio-information pieces judged to have been measured by the first device, and a second data group representing a plurality of bio-information pieces judged to have been measured by the second device.

With the above structure, the data processing device is able to make a distinction between bio-information acquired by both a first device licensed for manufacture by certain organizations and an unlicensed second device even when bio-information from both devices is intermingled, by displaying the bio-information on the same screen using different display modes.

BRIEF DESCRIPTION OF DRAWINGS

FIG. 2 shows an example of the data structure of a device information table T100.

FIG. 4 shows an example of the data structure of a display information table T200.

FIG. 5 explains distance calculation.

FIG. 13 shows a display method of the present invention.

DETAILED DESCRIPTION OF INVENTION

Embodiments of the present invention are described below with reference to the drawings.

1. First Embodiment 1.1 Regarding a Data Processing System 1

Figure 1:
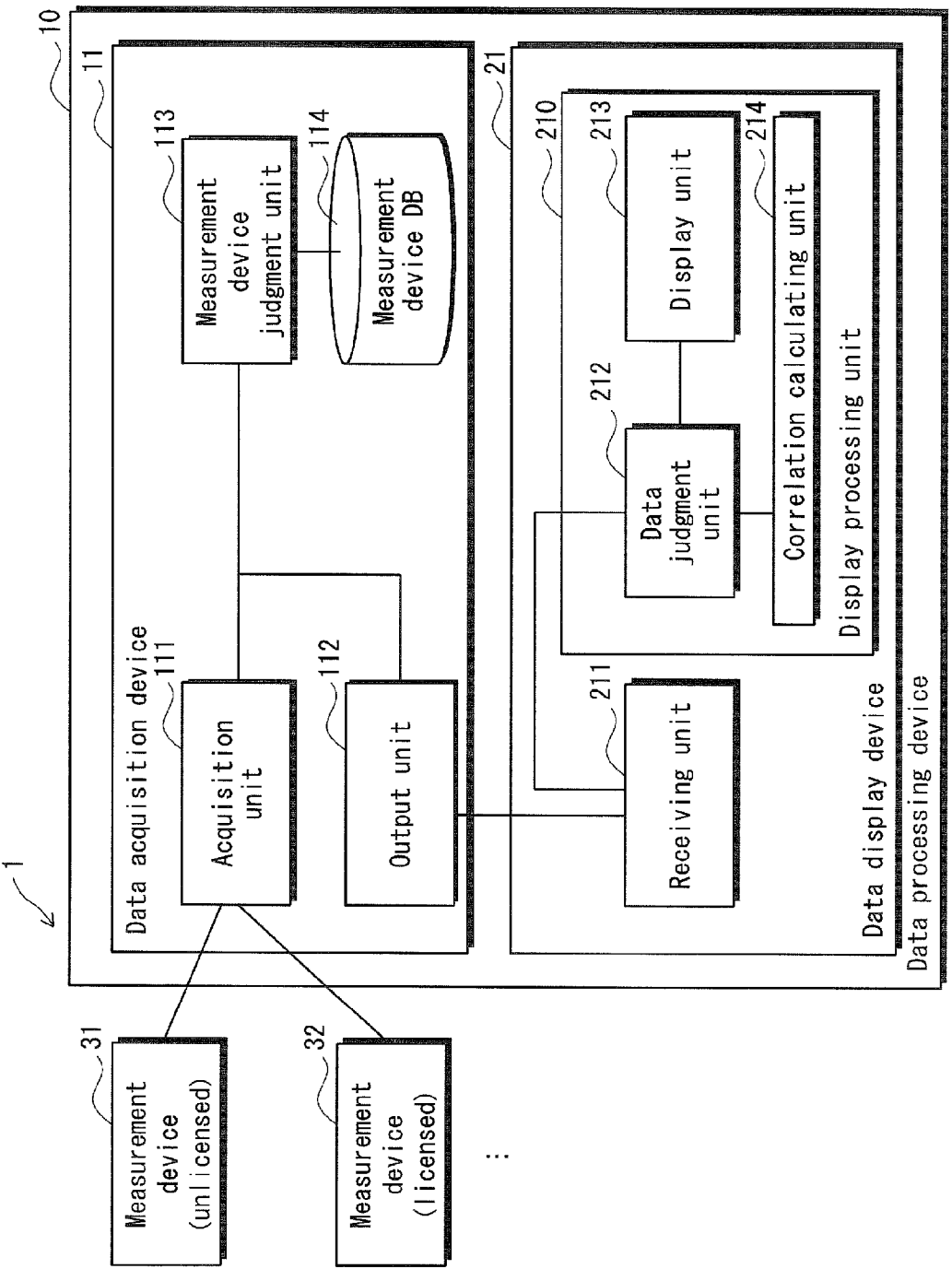
FIG. 1 is a block diagram showing the structure of a data processing system 1 and the structure of a data processing device 10.

FIG. 1 is a diagram showing the structure pertaining to the data processing system 1 of Embodiment 1. The data processing system 1 includes a data processing device 10 and measurement devices 31 and 32.

The measurement device 31 is a device unlicensed for medical use by specific organizations, and measures stress. The measurement device 31 could be, for example, a simple pulse measuring instrument focusing on pulse waves that change in response to stress. Alternatively, the measurement device 31 could be a low frequency condenser microphone focusing on how breathing changes in response to stress.

The measurement device 32 is a device licensed for medical use by specific organizations, and measures stress. The measurement device 32 could be, for example, a salivary amylase measuring device focusing on how levels of amylase in saliva change in response to stress.

The data processing device 10 acquires a plurality of user measurement results (hereafter, "bio-information") from measurement devices 31 and 32 and displays the bio-information measured by measurement device 32 (licensed) and the bio-information measured by device 31 (unlicensed), using different display modes so as to distinguish between the separate devices.

Note that, for the method of connecting measuring devices 31 and 32 to the data processing device, a USB (Universal Serial Bus) connection or wireless Bluetooth connection may be used.

1.2 Structure of the Data Processing Device 10

The structure of the data processing device 10 will now be explained.

As shown in FIG. 1, the data processing device 10 includes a data acquisition device 11 and a data display device 21.

Note that the data acquisition device 11 and the data display device 21 are connected by an internal bus.

(1) The Data Acquisition Device 11

The data acquisition device 11 acquires bio-information from the measurement devices 31 and 32 and identifies which device the bio-information came from. The data acquisition device 11 then sends the results of the identification along with the acquired bio-information to the data display device 21.

In further detail, the data acquisition device 11 includes an acquisition unit 111, an output unit 112, a measurement device identifying unit 113 and a measurement device DB (Data Base) 114, as shown in FIG. 1.

(1-1) The Measurement Device DB 114

The measurement device DB 114 stores information regarding licensed devices, and includes a device information table T100 as shown in FIG. 2.

The device information table T100 includes areas for storing a plurality of groups (hereafter, device information) made up of a device name, a model number, a measurement classification, a unit, an authorization flag, and an authorization number.

The device name indicates the name of a device. The model number is the number used to uniquely identify the device. The measurement classification indicates the kind of bio-information being measured with the device (for example, stress). The unit indicates the unit of measurement used. Further, the authorization number is used to uniquely identify a licensed device, and to indicate to a medical profession that the criteria for use in making medical judgments have been met. The authorization flag is a flag which shows whether the device in question has received authorization or not. For example, a value of "1" indicates that authorization has been received, and a value of "0" indicates that authorization has not been received. If the device in question has received authorization from a specific institution, an authorization number is granted to uniquely identify the licensed device. Note that, even if the authorization flag value is set at "1", if the authorization number is unknown, then the authorization number heading for the device information will be blank.

(1-2) The Acquisition Unit 111

The acquisition unit 111 acquires bio-information from measurement devices 31 and 32 which are connected to the acquisition unit 111 via a USB or wireless connection.

In more detail, the acquisition unit 111 acquires identifying information from measurement devices 31 and 32 which identifies the bio-information, the bio-information measurement date and time, and the device in question. In the present embodiment, a plurality of similar bio-information (for example, relating to stress) are acquired for the same person from measurement devices 31 and 32. The measurement date and time of the bio-information is also acquired. The identifying information here is the device name, device number and authorization number. The identifying information from the unlicensed measurement device 31 does not contain an authorization number. Also, even if a device is licensed, if the authorization number is unclear, the identifying information will not include an authorization number. The identifying information is acquired once for every group of pieces of bio-information acquired from each measurement device.

The acquisition unit 111 outputs, to the data display device 21 via the output device 112, display information including the acquired bio-information and corresponding measurement date and time and the results of identification by the measurement device identifying unit 113. Note that, in the following, the display information includes: a plurality of pieces of bio-information, a corresponding measurement date and time, identification results, and also a classification of the bio-information, the name of the device which measured the bio-information, and the units of measured value.

(1-3) The Measurement Device Identifying Unit 113

The measurement identifying unit 113 identifies, using the device information table T100 of the measurement device DB 114, whether each piece of bio-information acquired with the acquisition unit 111 came from a licensed device or not.

The measurement device identifying unit 113 identifies, by searching the device information table T100 using the identifying information acquired with the acquisition unit 111, whether the measurement device which outputted the plurality of bio-information is a licensed device or an unlicensed device.

(1-4) The Output Unit 112

The output unit 112 outputs the display information received from the acquisition unit 111 to the data display device 21.

(2) The Data Display Device 21

Regarding the bio-information outputted from the data acquisition device 11, the data display device 21 displays a plurality of pieces of bio-information measured by measurement device 32 (licensed) and a plurality of pieces of bio-information measured by measurement device 31 (unlicensed) in different display modes, according to the identification results from the measurement device identifying unit 113.

The data display device 21 consists of a display processing unit 210 and receiving unit 211, as shown in FIG. 1.

(2-1) The Receiving Unit 211

The receiving unit 211 receives display information outputted from the data acquisition device 11, and outputs the received display information to the display processing unit 210.

(2-2) The Display Processing Unit 210

When the plurality of bio-information included in the received display information has been measured by measurement device 31, in other words, by an unlicensed device, the display processing device 210 revises the aforementioned bio-information using the bio-information received from a licensed device as a standard, and displays the revised bio-information in such a way as to distinguish between the revised bio-information and the bio-information measured by the licensed device.

In more detail, the display processing unit 210 includes a data judging unit 212, a display unit 213, and a correlation calculating unit 214, as shown in FIG. 1.

(2-2-1) The Data Judgment Unit 212

The data judgment unit 212 judges the validity of the display information received with the receiving unit 211. Also, the data judgment unit 212 determines the display format of the corresponding bio-information in accordance with the identification results of the measurement device identifying unit 113.

In more detail, the data judgment unit 212 judges the validity of the display information based on whether or not each bio-information included in the display information received with the receiving unit 211 contains identification results.

Also, the data judgment unit 212 determines a layout wherein licensed bio-information and unlicensed bio-information are displayed in different colors or with a different rendering pattern so that a user can clearly differentiate between licensed bio-information (measured with a licensed device) and unlicensed bio-information (measured with an unlicensed device).

(2-2-2) The Correlation Calculating Unit 214

The correlation calculating unit 214 calculates the correlation between licensed bio-information and unlicensed bio-information, and revises the unlicensed bio-information using the licensed bio-information as a standard.

Figure 3:
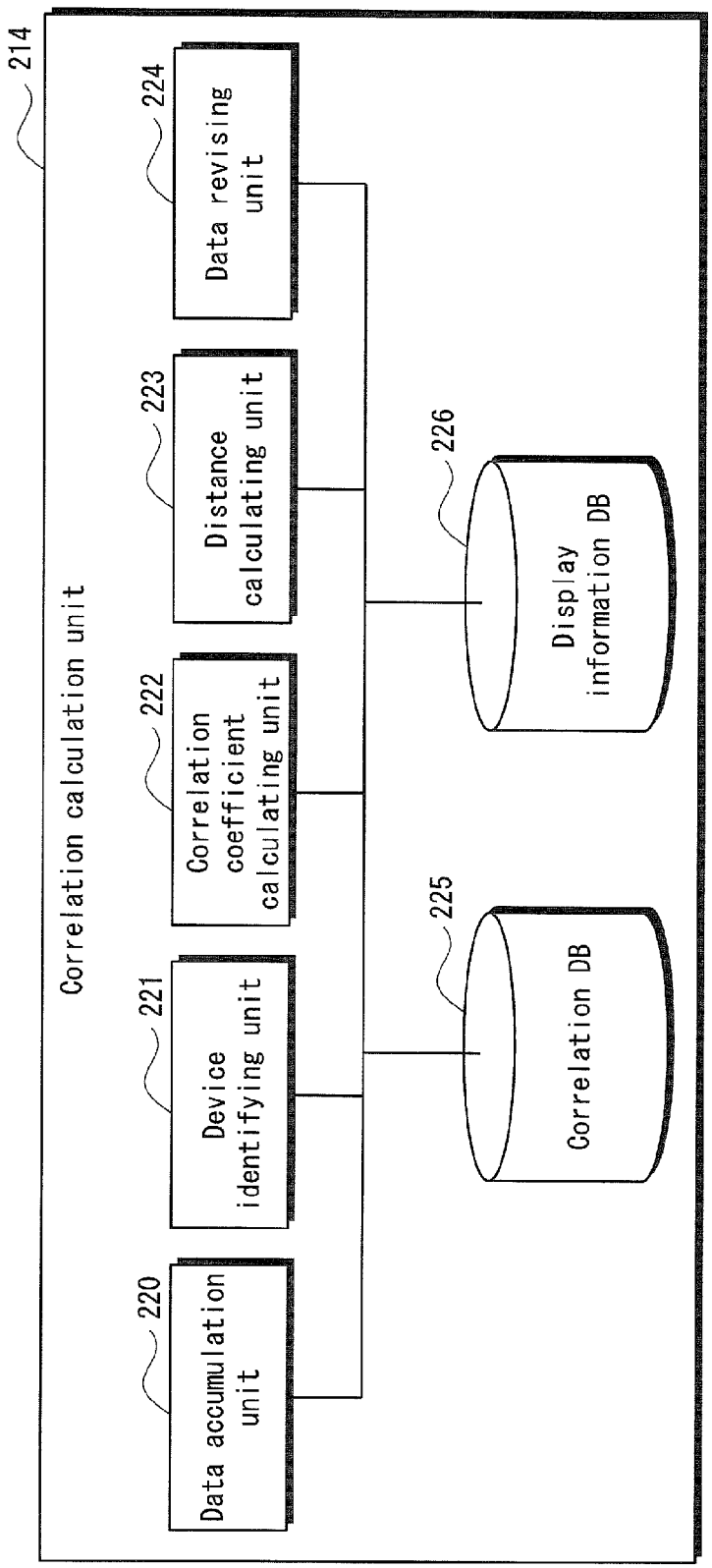
FIG. 3 is a block diagram showing the structure of a correlation calculating unit 214.

In more detail, the correlation calculation unit 214 is made up of a data accumulation unit 220, a device identifying unit 221, a correlation coefficient calculating unit 222, a distance calculating unit 223, a data revising unit 224, a correlation DB 225, and a display information DB 226, as shown in FIG. 3.

(a) The Data Accumulation Unit 220

The data accumulation unit 220 stores, in the display information DB 226, the display information which has been judged appropriate by the data judgment unit 212.

(b) The Device Identifying Unit 221

The device identifying unit 221 identifies which measurement devices measured the plurality of bio-information included in the display information accumulated with the data accumulation unit 220, using the device names included in the display information.

The device identifying unit 221 informs the correlation coefficient calculating unit 222 of the identification results.

For example, the device identifying unit 221 may identify measurement device 31 and measurement device 32 as different devices based on the device names included in the display information, and may identify the separate devices as, for example, "saliva amylase measuring instrument" and "simple pulse wave measuring instrument", respectively.

(c) The Information Display DB 226

The information display DB 226 stores display information. The display information is managed by the display information table T200 shown in FIG. 4. The display information table T200 includes areas for storing a plurality of groups made up of an information ID, an authorization flag, a measurement date and time, a classification, a measurement device name, and a measurement unit or measurement data, as shown in FIG. 4.

The information ID uniquely identifies each of a plurality of bio-information included in the display information stored by the display information table T200, and is assigned at the time of storage.

The display information includes various data stored within the authorization flags, measurement date and times, classifications, measurement device names, measurement units and measurement data.

In more detail, the identification results for the bio-information that was identified by the information ID and included in the display information, are stored within the authorization flag. A value of zero indicates measurement by an unlicensed device, and a value of 1 indicates measurement by a licensed device. Measurement date and time relating to the bio-information identified by the information ID is stored in the measurement date and time. The classification stores the classification of the bio-information. The device name included in the display information is stored in the measurement device name. The unit of the measured value included in the display information is stored in the measurement unit. Bio-information identified with the information ID included in the display information is stored in the measurement data.

(d) The Distance Calculating Unit 223

The distance calculating unit 223 compares bio-information from both licensed and unlicensed devices that are of the same classification and that are close in measurement date and time, then calculates the distance between both pieces of bio-information. Here, measurements are considered to be close in measurement date and time when using the date and time measured by one device as a standard, a measurement from another device was taken within 10 minutes either side of the standard.

In more detail, the distance calculating unit 223 calculates the distance between licensed bio-information and unlicensed bio-information using Equation 1 below.

$$\text{revised data}=a\times(\text{unlicensed bio-information})+b \quad \text{(Equation 1)}$$

Here, the revised data is data that shows the results of the unlicensed bio-information revised using the licensed bio-information as a standard.

The distance calculating unit 223 calculates "Distance=licensed bio-information−revised data", using Equation 1. Note that when there are a plurality of groups of licensed and unlicensed information close in measurement date and time, the distances of each will be calculated.

A detailed example of the distance calculation will be explained using FIGS. 4 and 5. The data of the information IDs from "0001" to "0009" of the display information table T200 of FIG. 4 are shown in the graph of FIG. 5. Data D10 to D15 indicate unlicensed bio-information, and data D20 to D23 indicate licensed bio-information. When using date and time measured by a licensed device as a standard, groups of bio-information close in measurement date and time according to FIGS. 4 and 5 are: information ID group "0001" and "0002" (data D10 and data D20), information ID group "0004" and "0005" (data D12 and D21), and information ID group "0007" and "0008" (data D14 and data D23). In this case, the distance calculating unit 223 calculates the distance between each of data D10 and D20, data D12 and D21, and data D14 and D23.

(e) The Correlation Coefficient Calculating Unit 222

The correlation coefficient calculating unit 222 calculates, by using the distance calculated by distance calculating unit 223, the correlation between licensed devices and unlicensed devices which measure bio-information of the same classification.

The following shows a detailed example of the calculation.

The correlation coefficient calculating unit 222 determines the value of coefficients a and b so as to minimize the sum of the distances, using each distance calculated by the distance calculating unit 223 from the use of the above formula.

The correlation coefficient calculating unit 222 stores a group (hereafter, correlation information), made up of the determined coefficients a and b, the bio-information classification, and the device names of each measurement device of licensed and unlicensed bio-information used to determine the coefficient in a correlation DB 225 which will be described below.

Note that, for situations where correlation is not calculated, the default settings of coefficients a and b may also be prepared in advance for each grouping of devices.

(f) The Correlation DB 225

The correlation DB 225 stores correlation information which includes the coefficients calculated by the correlation coefficient calculating unit 222, etc. The correlation information is managed in the correlation table T300 shown in FIG. 6.

Figure 6:
FIG. 6 shows an example of the data structure of a correlation table T300.

The correlation table T300 includes areas for storing a plurality of groups made up of the correlation ID, classifications, licensed devices, unlicensed devices, and the first coefficient and second coefficient, as shown in FIG. 6.

The correlation ID uniquely identifies correlation information filed in the correlation table T300, and is assigned at the time of filing.

The correlation information includes various data stored within the classifications, licensed measurement devices, unlicensed measurement devices, and first coefficient and second coefficient.

In more detail, the classification stores the classification of the bio-information. The licensed measurement device stores the name of the licensed measurement device included in the correlation information. The unlicensed measurement device stores the name of the unlicensed measurement device included in the correlation information. Furthermore, the first coefficient stores the coefficient a, and the second coefficient stores the coefficient b.

(g) The Data Revising Unit 224

The data revising unit 224 revises the unlicensed bio-information with the licensed bio-information as a standard, by using Equation 1 and the calculated coefficient a and coefficient b.

In more detail, the data revising unit 224 identifies a combination of licensed device and unlicensed device from the display information table T200. The data revising unit 224 determines the coefficient a and coefficient b from the correlation information which includes the identified combination. The data revising unit 224 uses the determined coefficient a and coefficient b and Equation 1 to revise the unlicensed bio-information included in the display information table T200.

(2-2-3) The Display Unit 213

The display unit 213 displays bio-information to a user in accordance with the display format determined with the data judging unit 212.

In more detail, the display unit 213 displays licensed bio-information and revised unlicensed bio-information in accordance with the layout determined with the data judgment unit 212, so that the two sets of bio-information can be differentiated between.

Figure 7:
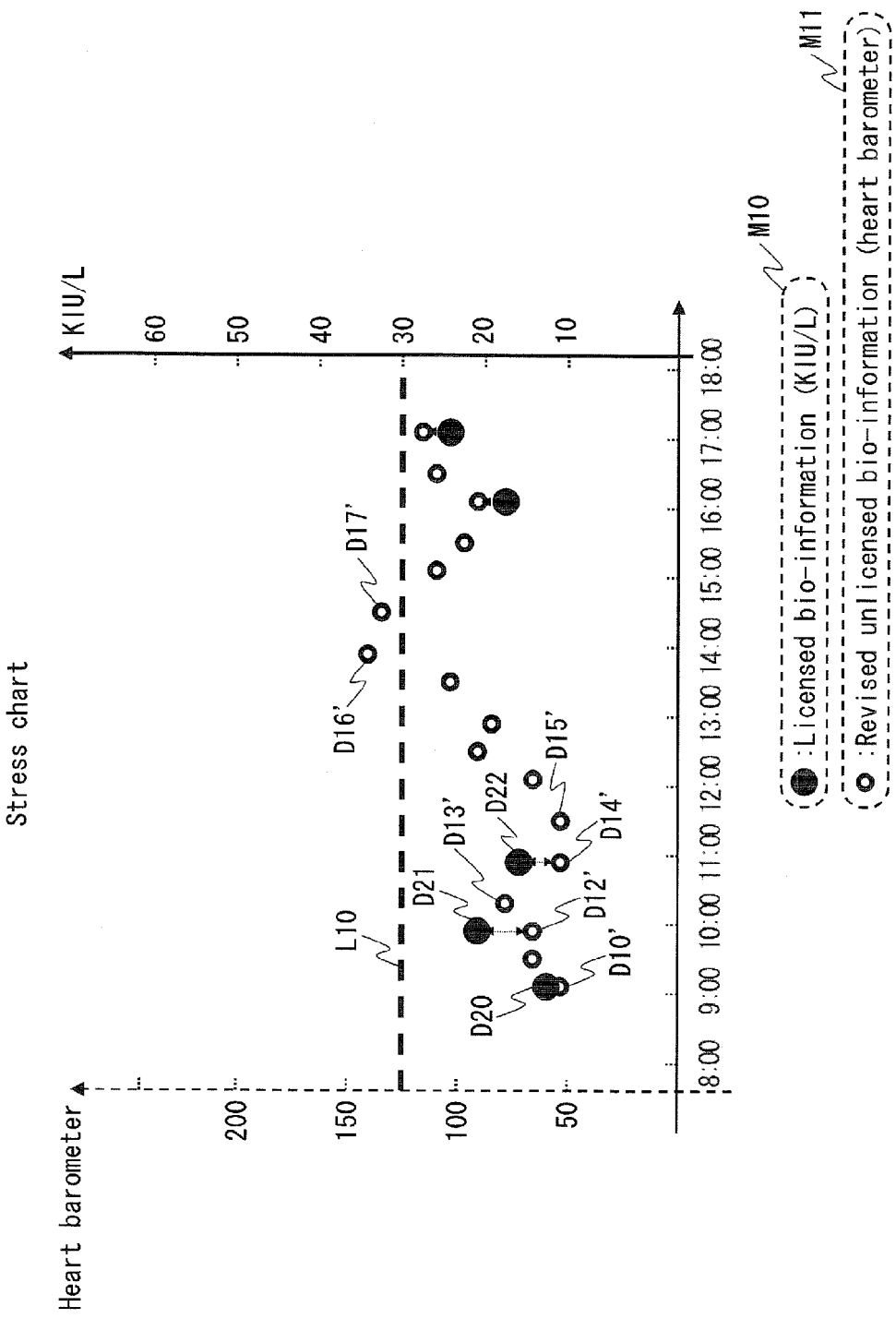
FIG. 7 shows an example of the display of a display unit 213.

One example of the display of the display unit 213 is shown in FIG. 7.

Data D20 to D22 are the same as the licensed bio-information shown in FIG. 5.

Data D10' to D15' is bio-information resulting from the revising of the data D10 to D15 shown in FIG. 4 using the numerical formula 1.

Also, a borderline L10 is a threshold value to determine whether or not there is an excess amount of stress. For example, the data D16' and D17' revised unlicensed bio-information is positioned higher than the threshold value, therefore at the measurement time of the bio-information, an excess of stress was considered to be present. In this way, by differentiating the display of licensed and unlicensed bio-information, it is possible to distinguish which data may and may not be used by a medical professional for making medical decisions. Also, as the unlicensed bio-information is less valid compared to that of licensed bio-information, the level of validity may be raised by performing revisions using the licensed bio-information as a standard.

1.3 The Operation of the Data Processing Device 10

(1) The Distinguishing Process

Here, when bio-information is acquired from a measuring device, the process used to distinguish whether the acquired measurement device is licensed or unlicensed will be described using the flowchart shown in FIG. 8.

The acquisition unit 111 acquires identifying information from the measurement device of the bio-information in question (step S5).

The measurement device identifying unit 113 determines whether or not an authorization number is included in the identifying information acquired by the acquisition unit 111 (step S10).

If it is determined that an authorization number is not included, ("No" in step S10), then the measurement device identifying unit 113 determines whether or not a device name included in the identifying information of the device information table T100 of the measurement DB 114 is present, and moreover, whether or not the authorization flag value is 1 (step S15). If a device name is present and, moreover, the authorization flag value is 1, ("Yes" in step S15), then the measurement device identifying unit 113 determines that the device indicated by the device name included in the identifying information is a licensed device (step S20). If there is no device name present, or if the authorization flag value is 0 ("No" in step S15), then the measurement device identifying unit 113 determines that the device indicated by the device name included in the identifying information is an unlicensed device (step S30).

If it is determined that an authorization number is included ("Yes" in step S10), the measurement device identifying unit 113 determines whether or not an authorization number is included in the device information table T100 of the measurement device DB 114 (step S25).

If it is determined that an authorization number is not included ("No" in step S25), the processing proceeds to step S15. If it is determined that an authorization number is included ("Yes" in step S25), the processing switches to step S20.

(2) Display Process

Figure 9:
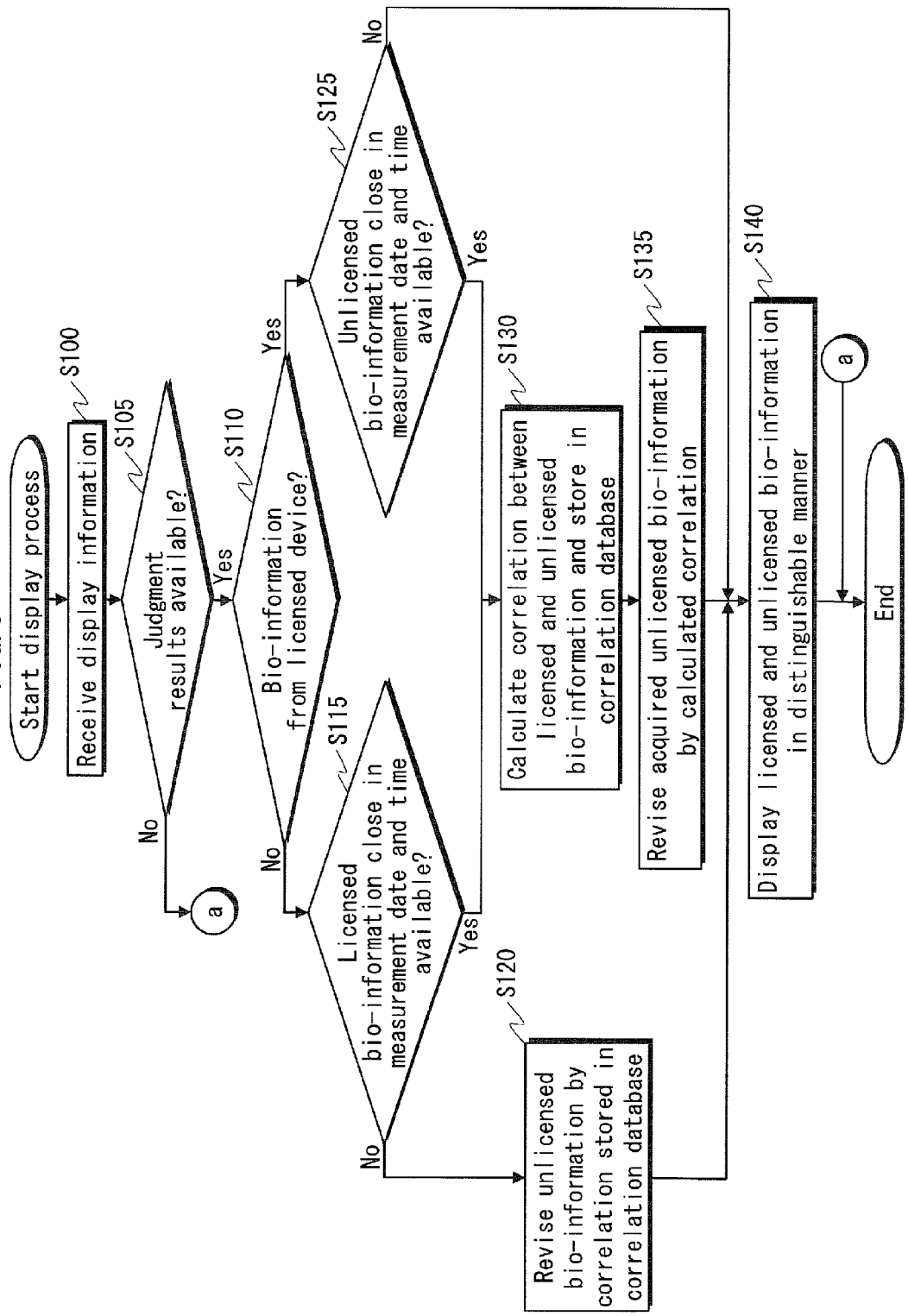
FIG. 9 is a flow diagram showing the operations of a display processing.

Here, a flowchart shown in FIG. 9 will be used to explain the display process of licensed bio-information and post-revision unlicensed bio-information.

The receiving unit 211 receives display information from the data acquisition device 11 (step S100).

The data judging unit 212 judges the validity of the display information by whether or not identification results exist for all bio-information included in the display information received by receiving unit 211 (step S105).

If the data judging unit 212 judges that identification results are not present ("No" in step S105), then the processing ends.

If the data judging unit 212 judges that identification results are present ("Yes" in step S105), the data accumulation unit 220 stores various data included in the display information in the display information DB 226. The device identifying unit 221 then judges whether or not a plurality of bio-information included in the display information accumulated by the data accumulation unit 220 was measured with a licensed device (step S110).

If the device identifying unit 221 judges that the bio-information did not come from a licensed device ("No" in step S110), then the correlation coefficient calculating unit 222 judges whether or not licensed bio-information close in measurement date and time is present in the display information table T200 (step S115). Note that this judgment is performed for all unlicensed bio-information included in the display information.

If the correlation coefficient calculating unit 222 judges that licensed bio-information close in measurement date and time is not present ("No" in step S115), then the data revising unit 224 revises the bio-information using the correlation information first coefficient and second coefficient included in the correlation table T300 of the correlation DB 225 (step S120). The correlation information used here shows the correlation between the display target device which measured licensed bio-information and the device which measured unlicensed bio-information. Furthermore, the display unit 213 displays the display target licensed bio-information and revised unlicensed bio-information in accordance with the layout determined by the data judging unit 212 (step S140).

If the correlation coefficient calculating unit 222 judges that licensed bio-information close in measurement date and time is present ("Yes" in step S115), then the distance calculating unit 223 calculates the difference between licensed and unlicensed bio-information close in measurement date and time. Furthermore, the correlation coefficient calculating unit 222 calculates the correlation (coefficients a, b) from the calculated distance, and files the correlation information including the calculated coefficients a, b to the correlation DB 225 (step S130). At this point, the distance calculating unit 223 calculates the distance of all groups of licensed and unlicensed bio-information close in measurement date and time.

The data revising unit 224 revises the display target unlicensed bio-information using the calculated coefficient a and b (step S135). The display unit 213 displays the display target licensed bio-information and revised unlicensed bio-information in accordance with the layout determined by the data judging unit 212 (step S140).

If the device identifying unit 221 judges that the bio-information is from a licensed device ("Yes" in step S110), then the correlation coefficient calculating unit 222 judges whether or not unlicensed bio-information close in measurement date and time is present in the display information table T200 (step S125). Note that this judgment is performed for all licensed bio-information included in the display information.

If the correlation coefficient calculating unit 222 judges that unlicensed bio-information close in measurement date and time is present ("Yes" in step S125), then the processing of step S125 continues. If the correlation coefficient calculating unit 222 judges that unlicensed bio-information close in measurement date and time is not present ("No" in step S125), then the processing of step S140 is performed.

1.4 Effects of Embodiment 1

With Embodiment 1, the data display device 21 displays bio-information measured with a licensed device and bio-information measured with an unlicensed device, the bio-information having been acquired from the data acquisition device 11, so that a user can clearly differentiate between the two. Also, the correlation between the licensed bio-information and unlicensed bio-information is calculated, and from the use of this correlation in revising the unlicensed bio-information, a higher-quality service is frequently provided. For example, with data relating to "stress", both bio-information outputted from a measurement device 32, which is a saliva amylase measuring instrument, and bio-information outputted from a measurement device 31, which is a simple pulse measuring instrument, may be intermingled and displayed, while the correlation between the two is also calculated and presented.

Generally, as unlicensed measurement devices do not have the restrictions necessary to achieve authorization, a generally higher frequency of measurement and use-anywhere functionality may be actualized compared to licensed devices; however, the reliability of the data gained can also be seen as inferior to that of licensed devices. Accordingly, it is possible to increase the reliability of unlicensed bio-information by using the correlation between unlicensed and licensed bio-information close in measurement date and time to revise the unlicensed bio-information using the licensed bio-information as a standard.

Also, by differentially displaying licensed and unlicensed bio-information, it is possible to tell upon sight which bio-information may be used as a basis for a medical professional to make medical decisions, and which may not. Furthermore, not only is it possible for a medical professional to use the borderline L10 shown in FIG. 7 in the use of licensed bio-information to make medical decisions, but also, by revising unlicensed bio-information using the correlation, when using only unlicensed bio-information, for example D11', D13', D15', D16' and D17', it is possible to make a significant comparison with the borderline L10 and for a user to confirm whether or not a state of excess stress has been entered.

[Embodiment 2]

Here the explanation will focus on the points of difference between a data processing device 1000 of Embodiment 2 and the data processing device 10 of Embodiment 1.

2.1 Regarding the Data Processing System 1A

Figure 10:
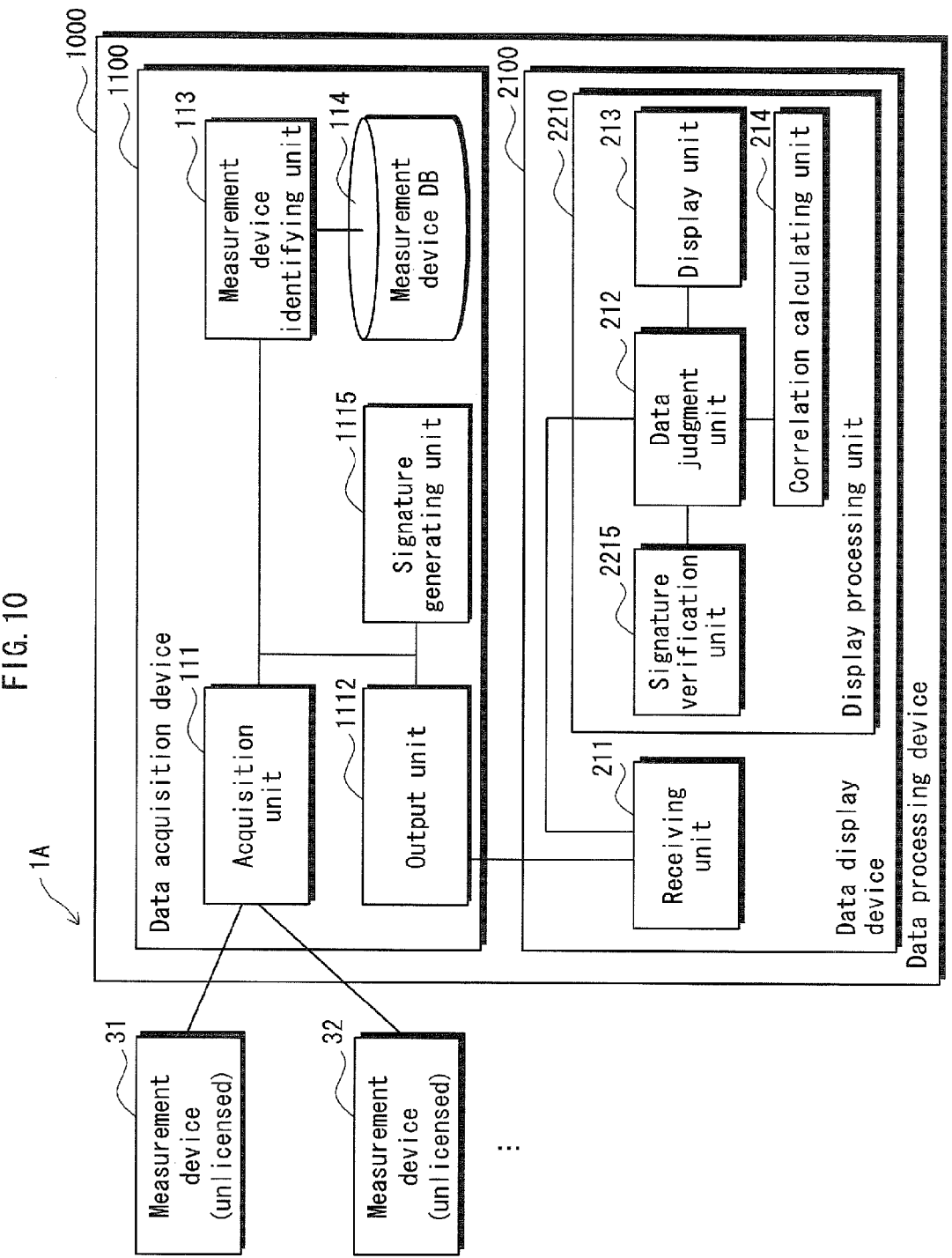
FIG. 10 is a block diagram showing the structure of a data processing system 1A and a data processing device 1000.

FIG. 10 is a diagram that shows the structure of the data processing system 1A of Embodiment 2. The data processing system 1A consists of the data processing device 1000 and measuring devices 31 and 32.

The data processing device 1000 consists of an acquisition device 1100 which acquires bio-information from a measuring device, and a data display device 2100 which displays the acquired bio-information, as shown in FIG. 10.

As licensed bio-information may be used by medical professionals to make medical decisions, any tampering with the content would cause an extremely serious problem. Therefore, when licensed bio-information is outputted from the data acquisition device 1100 to the data display device 2100, signature data is attached to show the validity of the information. Then, the data display device 2100 can verify whether or not the received licensed bio-information is valid by using the signature data.

2.2 The Structure of the Data Acquisition Device 1100 and the Data Display Device 2100.

The essential elements of the structure of the data acquisition device 1100 and the data display device 2100 will now be explained, however for those essential elements which are the same as those of Embodiment 1, the same numbers used in Embodiment 1 will be used and explanations will be omitted.

The structure of the data acquisition device 1100.

The data acquisition device 1100 consists of an acquisition unit 111, an output unit 1112, a measurement device judgment unit 113, a measurement device DB 114 and a signature generating unit 1115, as shown in FIG. 10.

The output unit 1112 and the signature generating unit 1115 will now be explained.

(1-1) The Signature Generating Unit 1115

The signature generating unit 1115 generates signature data for the display information when the measurement device judging unit 113 judges that each piece of bio-information included in the display information to be outputted to the data display device 2100 was measured with a licensed measurement device (measurement device 32 in this case).

In more detail, the signature generating unit 1115 calculates a hash value for the display information, and encrypts the calculated hash value with a private key for public key encryption. The encrypted hash value is the signature data.

(1-2) The Output Unit 1112

The output unit 1112 outputs the display information acquired from the acquisition unit 111 to the data display device 2100. Note that when signature data is generated with the signature generating unit 1115, the signature data is outputted along with the display information to be outputted.

(2) The Structure of the Data Display Device 2100

The data display device 2100 consists of a receiving unit 2211 and a display processing unit 2210, as shown in FIG. 10. The display processing unit 2210 consists of a data judgment unit 212, a display unit 213, a correlation calculation unit 214 and a signature verification unit 2215.

The receiving unit 2211 and the signature verification unit 2215 will now be explained.

(2-1) The Receiving Unit 2211

The receiving unit 2211 receives display information outputted from the data acquisition device 1100, and outputs the received display information to the display processing unit 2210. At this point, the receiving unit 2211 also outputs signature data to the display processing unit 2210 when signature data is attached to the display information.

(2-2) The Signature Verification Unit 2215

The signature verification unit 2215 verifies the validity of the display information using the signature data attached to the display information, when the data judgment unit 212 judges that the plurality of pieces of bio-information included in the display information were measured by a licensed device.

In more detail, the signature verification unit 2215 decrypts the signature data using the public key which corresponds to the private key used in the generation of the signature data, and calculates the hash value of the display information, then comparing the decrypted results with the calculated hash value. If the decrypted results comply with the calculated hash value, the display information is judged to be valid, and if they do not comply, the display information is judged to be invalid.

2.3 Operations

Here, the operations of the data processing device 1000 will be explained.

(1) The Judgment Process

Figure 8:
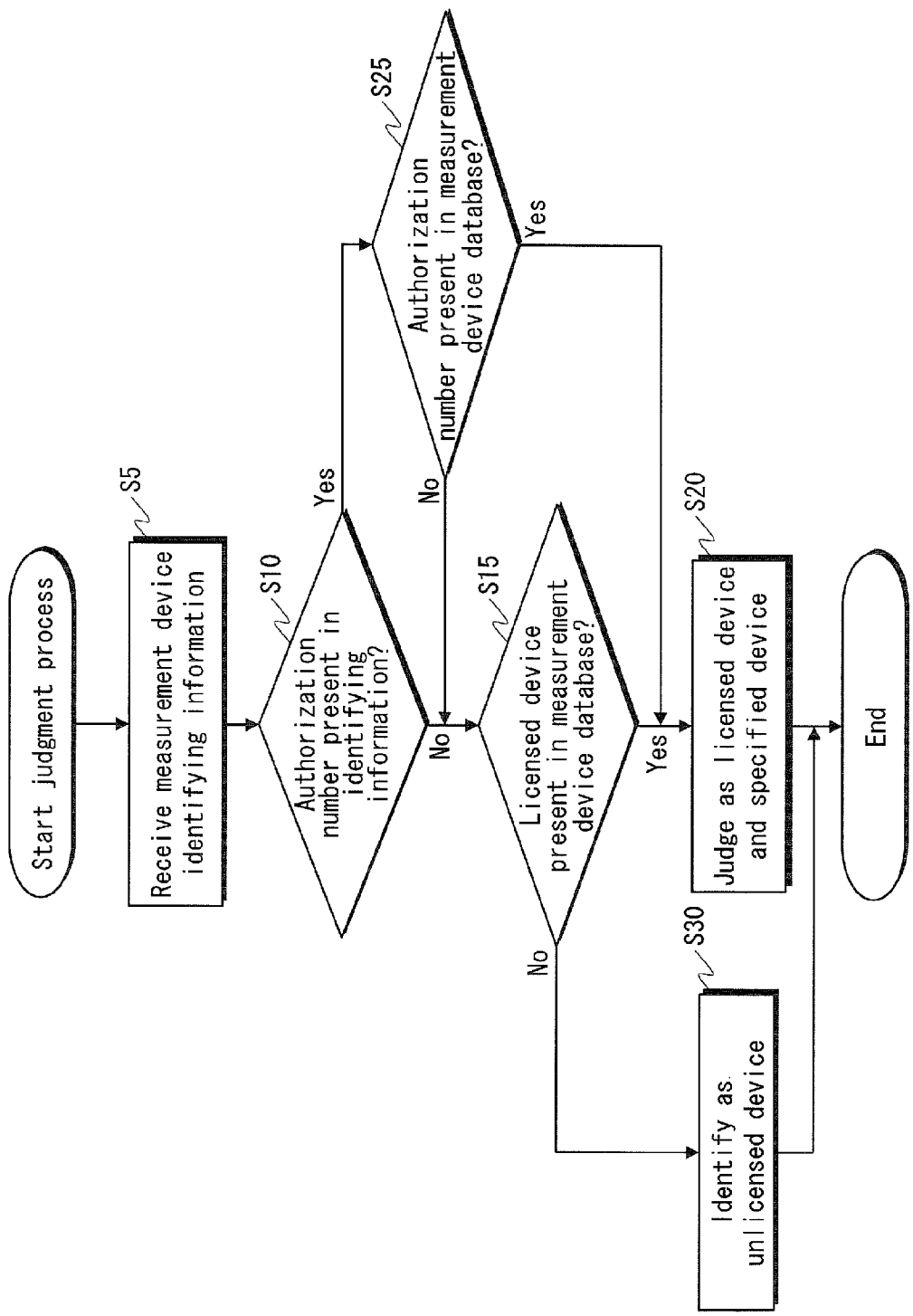
FIG. 8 is a flow diagram showing the operations of a judgment processing.

The judgment process is the same as the process shown in FIG. 8, therefore an explanation will be omitted here.

(2) The Output Process

Figure 11:
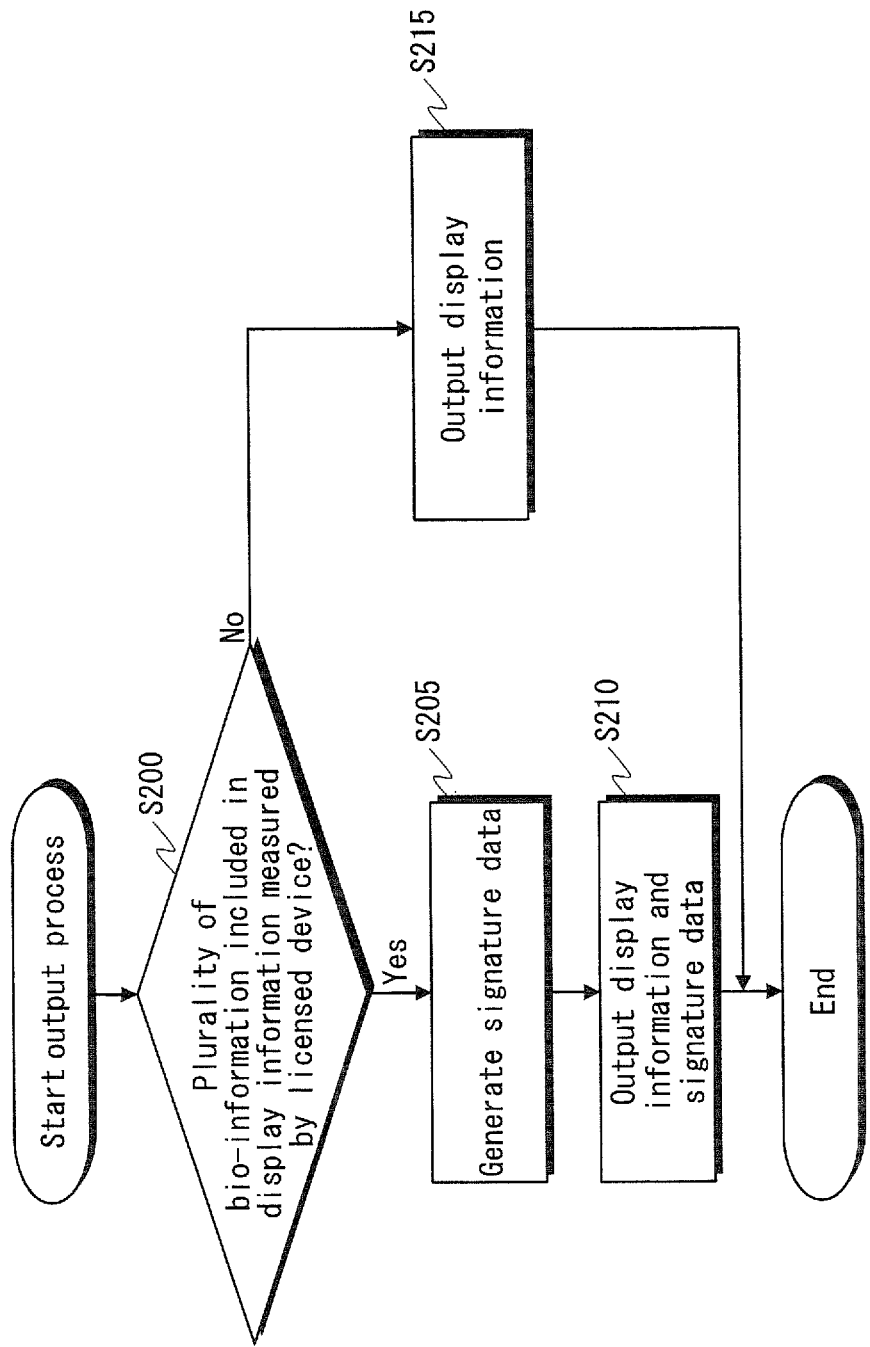
FIG. 11 is a flow diagram showing the operations of an output processing.

Here, the process when display information is outputted to the data display device 2100 from the data acquisition device 1100 will be explained using the flow diagram shown in FIG. 11.

The signature generating unit 1115 judges whether or not each piece of bio-information included in the display information to be outputted was measured by a licensed device (step S200). In more detail, the signature generating unit 1115 performs according to the result of the judgment by the measurement device judgment unit 113.

When judging that the measurement was made with a licensed device ("Yes" in step S200), the signature generating unit 1115 then generates signature data for the display information (step S205).

The output unit 1112 outputs the display information and the signature data for that display information to the data display device 2100 (step S210).

When the signature generating unit 1115 judges that the measurement was not made with a licensed device ("No" in step S200), then the output unit 1112 outputs the display information to the data display device 2100 (step S215).

(3) The Display Processing

The display processing is achieved by performing signature verification in advance of the process of step S125 when the answer to step S100 in the flow diagram shown in FIG. 9 is "Yes".

2.4 Effects of Embodiment 2

Embodiment 2 has the effects shown by Embodiment 1.

Furthermore, the validity regarding the licensed bio-information is guaranteed, and the data can be used without concern in making medical judgments.

3. Modifications

The present invention is not limited to the embodiments described above. For example, the following modifications may be considered.

(1) In the embodiments above, when bio-information is outputted from the measurement device to the data acquisition device, signature data may be attached to the bio-information. In this case, the data acquisition device performs verification using the received signature data, and when a judgment is made from the verification results that the received bio-information is valid, the data acquisition device outputs to the data display device the display information which includes the bio-information. When a judgment is made that the bio-information is invalid, processing is canceled.

Also, the measurement device may encrypt the bio-information outputted to the data acquisition device. In this case, the data acquisition device decrypts the received encrypted bio-information, and when decryption can be performed normally, outputs the display information that includes the bio-information to the data display device. When decryption cannot be performed normally, the processing is canceled.

(2) In the above embodiments, a same component (in this case, the data processing device) includes a data acquisition device and a data display device, and the connection configuration is a connection with an internal bus. However, the connection configuration is not limited to that of the above embodiments, and other connection configurations might include connection by, for example, a network (internet), USB, or Bluetooth. With network (internet), USB or Bluetooth connections, the data acquisition device and data display device do not need to be included in a same component, and in other words may be placed in separate locations.

Particularly, in Embodiment 2 above, connection with one of either an internet connection, USB connection or Bluetooth connection makes the need for the attachment of signature data greater. The reason for this is that when display information is inputted/outputted with an internet, USB or Bluetooth connection, the likelihood of a leak to a malicious third-party is greater than when input/output is performed using an internal bus.

(3) In the above embodiments, Equation 1 is used when calculating a correlation coefficient or revising unlicensed bio-information, but the calculation and revision are not limited to this.

The following Equation 2 for an obtainable distance number n (where n is a natural number) may also be used.

$$\text{Revised data} = a_n \times (\text{unlicensed bio-information})^n + a_{(n-1)} \times (\text{unlicensed bio-information})^{(n-1)} + \ldots + a_1 \times (\text{unlicensed bio-information}) + a_0, \quad \text{(Equation 2)}$$

Also, as long as a relationship between licensed and unlicensed bio-information can be defined, Equations 1 or 2 need not be used.

(4) The above embodiments use an authorization number and authorization flag to identify whether a device is licensed or unlicensed, but the present invention is not limited to this.

An authorization number alone may be used, or an authorization flag alone may be used.

Also, an authorization number or authorization flag does not necessarily need to be used. Any means that can identify whether a device is licensed or unlicensed may be used.

(5) In the above embodiments, the device used to measure stress is a simple pulse measuring instrument, a low frequency condenser microphone, or a salivary amylase measuring device, but the present invention is not limited to these devices, and another device for measuring stress may be used.

(6) In the above embodiments, the bio-information relates to stress, but the bio-information is not limited to this.

Bio-information is suitable as long as it is related to the monitoring of human health, such as blood pressure, blood sugar levels, body temperature, etc.

(7) In the above embodiments, when both kinds of bio-information are being displayed, the M10 and M11 messages inside the broken lines of FIG. 7 may be displayed along with the stress chart, in order for the display mode to show which bio-information was measured by which device. Alternatively, either one of the M10 or M11 messages may be displayed.

(8) In the above embodiments, when calculating distance, the period of time for bio-information to be acquired is within ten minutes either side of the date and time used as the standard measured by one device, however, the present invention is not limited to this.

The breadth of time may be changed to fit the user, the user device, or the type of bio-information.

(9) A program listing steps for the methods described in the above embodiments may be stored in a memory. A Central Processing Unit (CPU) or the like may read the programs from memory and execute the read programs in order to achieve the above methods.

The program listing the steps for the above methods may also be stored on a recording medium and distributed.

(10) Each structure in the above embodiments may be implemented as a Large Scale Integration (LSI), which is a type of integrated circuit. These structures may respectively be made into discrete chips, or part or all of the structures may be made into one chip. Although referred to here as an LSI, depending on the degree of integration, the terms Integrated Circuit (IC), system LSI, super LSI, or ultra LSI are also used. Furthermore, the method of integration is not limited to LSI. Integration may be achieved via a dedicated circuit or a general-purpose processor. Alternatively, a Field Programmable Gate Array (FPGA), which is an LSI that can be programmed after manufacture, or a reconfigurable processor, which is an LSI whose connections between internal circuit cells and settings for each circuit cell can be reconfigured, may be used. Furthermore, calculation by these functional blocks may be performed using, for example, a Digital Signal Processor (DSP) or CPU. These processing steps may be recorded on a recording medium as a program and executed in order to perform the above processing.

Additionally, if technology for integrated circuits that replaces LSI emerges, owing to advances in semiconductor technology or to another derivative technology, the integration of functional blocks may naturally be accomplished using such technology. The application of biotechnology or the like is possible.

Figure 12:
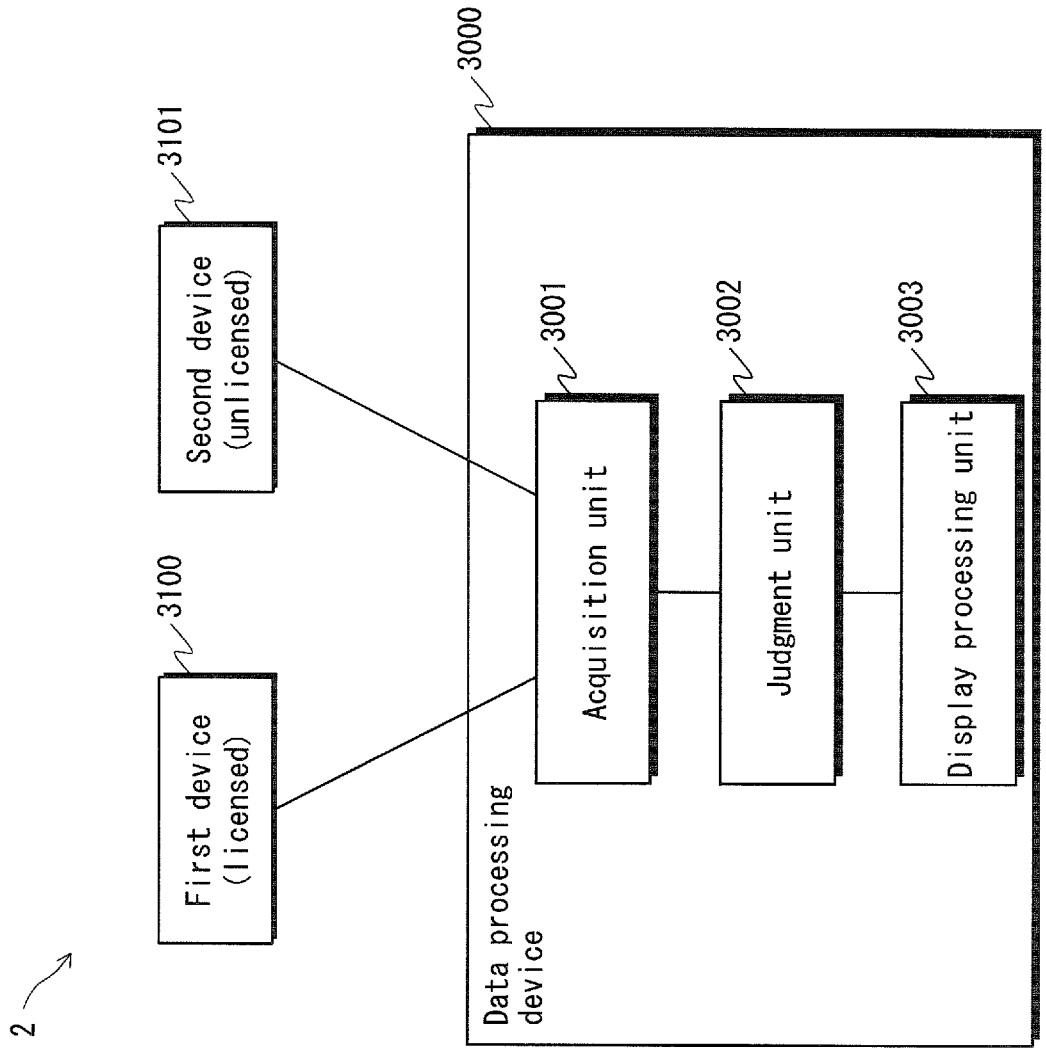
FIG. 12 shows the structure of a data system 2 and a data processing device 3000 of the present invention.

(11) The data processing device 3000 of the present invention, as shown in FIG. 12, may have a structure including: (i) an acquisition unit 3001 which acquires a plurality of pieces of bio-information of a same category and from a same person, the bio-information measured with both a licensed first device 3100 that is medically licensed for manufacture by certain organizations, and an unlicensed second device 3101, (ii) a judgment unit 3002 which judges whether each acquired piece of bio-information was measured by the first device 3100 or by the second device 3101, and (iii) a display processing unit 3003 which displays with different display modes on a same screen, a first data group ascribable to a plurality of bio-information judged to have been measured with the first device 3100, and a second data group ascribable to a plurality of bio-information judged to have been measured with the second device 3101.

In this case, the acquisition unit 3001 may be achieved with the acquisition unit 111 shown in Embodiments 1 and 2, and the judgment unit 3002 may be actualized with a combination of the measurement device judgment unit 113 and measurement device DB 114 shown in Embodiments 1 and 2. Also, the display processing unit 3003 may be actualized with the display processing unit 210 shown in Embodiment 1 and the display processing unit 2210 shown in Embodiment 2.

(12) The data processing system 2 of the present invention, as shown in FIG. 12, may consist of a licensed first device 3100 that is medically licensed for construction by certain organizations, an unlicensed second device 3101, and a data processing device 3000. The structural components of the data processing device 3000 have already been described, so an explanation will be omitted here.

(13) The display processing method pertaining to the present invention used by the data display device provided with an acquisition unit, judgment unit and display processing unit as shown in FIG. 13 may include: (i) an acquisition step (step S300) where the acquisition unit acquires a plurality of a same category of bio-information from a same person, the bio-information measured with both a licensed first device that is medically licensed for construction by certain organizations, and an unlicensed second device, (ii) a judgment step (step S305) where the judgment unit judges whether each piece of bio-information acquired in the acquisition step was measured by the first device or by the second device, and (iii) a display processing step (step S310) where the display processing unit displays with different display modes on a same screen, a first data group ascribable to a plurality of bio-information judged to have been measured with the first device, and a second data group ascribable to a plurality of bio-information judged to have been measured with the second device.

(14) The above Embodiments or modifications may be combined.

4 Supplementary Explanation (1) In one embodiment of the present invention, a data processing device comprises: an acquisition unit acquiring a plurality of pieces of a same category of bio-information about a same person, the bio-information measured with both a licensed first device and an unlicensed second device; a judgment unit that judges whether each acquired piece of bio-information acquired in the previous acquisition was measured by the first device or by the second device; and a display processing unit that displays with different display modes on a same screen, a first data group of a plurality of pieces of bio-information judged to have been measured with the first device, and a second data group of a plurality of pieces of bio-information judged to have been measured with the second device.

With this structure, because the data processing device displays with different display modes on the same screen the bio-information measured with both a licensed first device that is medically licensed for construction by certain organizations and an unlicensed second device, it is possible to identify the data even though both kinds of bio-information are intermingled. A user of the data processing device, for example, a medical professional, will be able to identify which bio-information may and may not be used to make medical decisions. Also, a user taking measurements will be able to monitor their own health from the changes shown by the licensed bio-information and unlicensed bio-information.

(2) Here, the display processing unit may use a correlation between the information measured with the first device and the second device to revise bio-information measured with the second device using bio-information measured with the first device as a standard, and may display a data group made up of revised bio-information as the second data group.

With this structure, the data processing device is able to revise the bio-information from an unlicensed device using the bio-information from a licensed device as a standard, therefore raising the reliability of the bio-information from the unlicensed device.

(3) Here, the acquisition unit may acquire, with the bio-information, an identifier that identifies the measurement device, and the judgment unit may identify the acquired bio-information, by identifying, based on the identifier, whether the device shown by the identifier is licensed or not.

With this structure, by identifying whether the device is licensed or not, the data processing device is able to identify the acquired bio-information.

(4) Here, the identifier for the first device indicates authorization by a certain institution, and is an authorization number attached to the first device, the acquisition unit further acquires signature data for the authorization number, and the judgment unit performs verification of the signature data, and when the judgment unit judges from the verification results that the authorization number is valid, judges that the corresponding bio-information was measured with the first device.

With this structure, the data processing device confirms the validity of the corresponding authorization number by performing signature verification. By doing so, it is possible to confirm whether or not the authorization number has been falsified, therefore, it is possible to increase the reliability of the fact that the first measurement device is a licensed device.

(5) The data processing device includes a data acquisition device provided with the acquisition unit and the judgment unit, and a data display device provided with the display processing unit, the data acquisition device and the data display device are connected via internet, when outputting the plurality of pieces of bio-information acquired by the data acquisition device from the first and second devices and the judgment results of the judgment unit to the data display device, the data acquisition device attaches a signature to the bio-information that the judgment unit has judged to have been measured with the first device, and the data display device carries out display with the display processing unit only when the bio-information of the signature verification that used the signature data has been judged valid.

With this structure, when the data acquisition device of the data processing device outputs the bio-information measured with the first device to the data processing device, signature data is attached. Therefore, it is possible to prevent falsification of the bio-information on the route from the data acquisition device to the data display device. With this, it is possible to increase the reliability of the bio-information measured with the first device. Therefore, a medical professional for example would be able to use, to make medical judgments, bio-information measured by a first device that can be relied upon not to be falsified.

(6) Here, the display processing unit also displays identification information that identifies whether the bio-information shown in each display mode was measured by the first device or the second device, when the display processing unit displays the first data group and second data group.

With this structure, when the data processing device displays the first data group and second data group, because identification information is displayed that identifies which device measured the bio-information shown in each display mode, a person viewing the data groups (such as a medical professional) will be able to easily identify the data groups).

(7) Also, another embodiment of the present invention has a data processing system made up of a first device that is a medical device licensed for manufacture by a certain institution; an unlicensed second device; and a data processing device, wherein the first device and second device measure a same category of bio-information, and the data processing device comprises: an acquisition unit that acquires a plurality of pieces of a same category of bio-information from a same person, the bio-information measured with both a licensed first device and an unlicensed second device, a judgment unit that judges whether each piece of bio-information acquired in the previous acquisition step was measured by the first device or by the second device, and a display processing unit that displays with different display modes on a same screen, a first data group ascribable to a plurality of pieces of bio-information judged to have been measured with the first device, and a second data group ascribable to a plurality of pieces of bio-information judged to have been measured with the second device.

With this structure, because the data processing system displays with different display modes on a same screen the bio-information measured with both a licensed first device that is medically licensed for construction by certain organizations and an unlicensed second device, it is possible to identify the data even though both kinds of bio-information are intermingled. With this, a user of the data processing device, for example, a medical professional, will be able to identify which bio-information may and may not be used to make medical decisions. Also, a user taking measurements will be able to monitor their own health from the changes shown by the licensed bio-information and unlicensed bio-information.

The present invention is useful in devices that acquire and display information for monitoring human health.

[Reference Signs List]
1, 1A Data processing system
10, 1000 Data processing device
11, 1100 Data acquisition device
21, 2100 Data display device
31 Measurement device
32 Measurement device
111 Acquisition unit
112, 1112 Output unit
113 Measurement device identifying unit
114 Measurement device database
210, 2210 Display processing unit
211, 2211 Receiving unit
212 Data judgment unit
213 Display unit
214 Correlation calculating unit
220 Data accumulation unit
221 Device identifying unit
222 Correlation coefficient calculating unit
223 Distance calculating unit
224 Data revising unit
225 Correlation DB
226 Display information DB
1115 Signature generating unit
2215 Signature verification unit
2 Data processing system
3000 Data processing device
3001 Acquisition unit
3002 Judgment unit
3003 Display processing unit
3100 First device
3101 Second device

The invention claimed is:

1. A data processing device comprising:
a non-transitory memory device storing a program; and
a hardware processor configured to execute the program and cause the data processing device to operate as the following units stored in the memory device:
an acquisition unit that acquires, from a first measurement device that is a medical device for which a manufacturing license has been granted by a medical organization, bio-information pieces measured by the first measurement device along with a device ID that identifies the first measurement device, and, from a second measurement device that is a medical device for which a manufacturing license has not been granted by the medical organization, bio-information pieces measured by the second measurement device along with a device ID that identifies the second measurement device, both the bio-information pieces measured by the first measurement device and the bio-information pieces measured by the second measurement device being bio-information pieces of a single category about a single person;
a judgment unit that judges whether each acquired bio-information piece is authorized bio-information or unauthorized bio-information, by determining, using the device ID acquired along with the bio-information piece, whether the bio-information piece was measured by the first measurement device or by the second measurement device; and
a display processing unit that displays on a same screen, with different graph representations, a first data group representing a plurality of bio-information pieces judged to be authorized bio-information by the judgment unit, and a second data group representing a plurality of bio-information pieces judged to be authorized bio-information by the judgment unit,
wherein the data processing device stores an authorization number associated with the first measurement device, and the judgment unit judges whether each acquired bio-information piece is authorized bio-information or unauthorized bio-information using the authorization number and the device ID acquired by the acquisition unit.

2. The data processing device of claim 1, wherein the display processing unit revises the unauthorized bio-information using the authorized bio-information as a standard, according to a correlation between the authorized bio-information and the unauthorized bio-information, and displays a data group made up of revised bio-information pieces as the second data group.

3. The data processing device of claim 1, wherein
when the device ID indicates the first device, the device ID indicates authorization by the medical organization, and is an authorization number associated with the first device,
the acquisition unit further acquires signature data for the authorization number, and
the judgment unit performs verification of the signature data, and when judging from the verification results that the authorization number is valid, judges, as a result of the verification, that the corresponding bio-information piece was measured by the first device.

4. The data processing device of claim 2, including:
a data acquisition device provided with the acquisition unit and the judgment unit, and a data display device provided with the display processing unit, wherein the data acquisition device and the data display device are connected via the Internet, when outputting to the display device the plurality of bio-information pieces acquired by the data acquisition device from the first and second devices, and the judgment results of the judgment unit, the data acquisition device adds a signature to the bio-information piece that the judgment unit has judged to be authorized bio-information, and the data display device carries out display with the display processing unit only when the bio-information piece corresponding to the signature verification based on the signature data has been judged valid.

5. The data processing device of claim 2, wherein the display processing unit also displays identifying information to show whether the bio-information pieces displayed with one of the graph representations were measured by the first device or the second device, when the display processing unit displays the first data group and second data group.

6. A data processing system comprising: a first measurement device that is a medical device for which a manufacturing license has been granted by a medical organization; a second measurement device that is a medical device for which a manufacturing license has not been granted by a medical organization; and a data processing device, wherein the first measurement device and the second measurement device measure a single category of bio-information, and the data processing device comprises:

a non-transitory memory device storing a program; and a hardware processor configured to execute the program and cause the data processing device to operate as the following units stored in the memory device:

an acquisition unit that acquires bio-information pieces measured by the first measurement device along with a device ID that identifies the first measurement device, and bio-information pieces measured by the second measurement device along with a device ID that identifies the second measurement device, both the bio-information pieces measured by the first measurement device and the bio-information pieces measured by the second measurement device being bio-information pieces of a single category about a single person;

a judgment unit that judges whether each acquired bio-information piece is authorized bio-information or unauthorized bio-information, by determining, using the device ID acquired along with the bio-information piece, whether the bio-information piece was measured by the first measurement device or by the second measurement device; and a display processing unit that displays on a same screen, with different graph representations, a first data group of a plurality of bio-information pieces judged to be authorized bio-information by the judgment unit, and a second data group of a plurality of bio-information pieces judged to be unauthorized bio-information by the judgment unit, wherein the data processing device stores an authorization number associated with the first measurement device, and the judgment unit judges whether each acquired bio-information piece is authorized bio-information or unauthorized bio-information using the authorization number and the device ID acquired by the acquisition unit.

7. A data processing method used in a data processing device that includes a non-transitory memory device storing a program, and a hardware processor configured to execute the program and cause the data processing device to operate as an acquisition unit, a judgment unit and a display processing unit stored in the memory so as to perform the data processing method, the data processing method comprising:

acquiring, using the acquisition unit and from a first measurement device that is a medical device for which a manufacturing license has been granted by a medical organization, bio-information pieces measured by the first measurement device along with a device ID that identifies the first measurement device, and, from a second measurement device that is a medical device for which a manufacturing license has not been granted by the medical organization, bio-information pieces measured by the second measurement device along with a device ID that identifies the second measurement device, both the bio-information pieces measured by the first measurement device and the bio-information pieces measured by the second measurement device being bio-information pieces of a single category about a single person;

judging, using the judging unit, whether each bio-information piece is authorized bio-information or unauthorized bio-information, by determining, using the device ID acquired along with the bio-information piece, whether the bio-information piece was measured by the first measurement device or by the second measurement device; and displaying, using the display processing unit and on a same screen, with different graph representations, a first data group of a plurality of bio-information pieces judged to be authorized bio-information by the judgment unit, and a second data group of a plurality of bio-information pieces judged to be unauthorized bio-information by the judgment unit, wherein the data processing method stores an authorization number associated with the first measurement device, and the judgment step judges whether each acquired bio-information piece is authorized bio-information or unauthorized bio-information using the authorization number and the device ID acquired by the acquisition step.

\* \* \* \* \*